(12) United States Patent
Morales et al.

(10) Patent No.: US 7,648,936 B2
(45) Date of Patent: Jan. 19, 2010

(54) SPRAY-DRIED TRANSITION METAL ZEOLITE AND ITS USE

(75) Inventors: Edrick Morales, West Chester, PA (US); Guoyi Fu, Ellicott City, MD (US); Roger A. Grey, West Chester, PA (US); Kun Qin, Chadds Ford, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 20 days.

(21) Appl. No.: 12/011,659

(22) Filed: Jan. 29, 2008

(65) Prior Publication Data

US 2009/0192323 A1 Jul. 30, 2009

(51) Int. Cl.
*B01J 29/04* (2006.01)
(52) U.S. Cl. .................. 502/66; 502/350; 502/242; 502/74; 549/533
(58) Field of Classification Search .............. 502/300, 502/350, 66; 549/533
See application file for complete search history.

(56) References Cited

U.S. PATENT DOCUMENTS

| | | | |
|---|---|---|---|
| 4,410,501 A | 10/1983 | Taramasso et al. | |
| 4,612,138 A | 9/1986 | Keiser | |
| 4,701,428 A | 10/1987 | Bellussi et al. | |
| 4,833,260 A | 5/1989 | Neri et al. | |
| 4,954,325 A | 9/1990 | Rubin et al. | |
| 4,954,653 A | 9/1990 | Bellussi et al. | |
| 5,354,875 A | 10/1994 | Nemeth et al. | |
| 5,403,513 A | 4/1995 | Sato et al. | |
| 5,500,199 A | 3/1996 | Bellussi et al. | |
| 5,965,476 A | 10/1999 | Balducci et al. | |
| 6,008,388 A | 12/1999 | Dessau et al. | |
| 6,077,498 A | 6/2000 | Diaz Cabañas et al. | |
| 6,106,803 A | 8/2000 | Hasenzahl et al. | |
| 6,114,551 A | 9/2000 | Levin et al. | |
| 6,420,437 B1 | 7/2002 | Mori et al. | |
| 6,465,382 B1 | 10/2002 | Strebelle et al. | |
| 6,524,984 B2 | 2/2003 | Carati et al. | |
| 6,551,546 B1 | 4/2003 | Grosch et al. | |
| 6,646,142 B1 | 11/2003 | Meima et al. | |
| 6,849,570 B2 | 2/2005 | Hasenzahl et al. | |
| 6,958,405 B2 | 10/2005 | Le-Khac et al. | |
| 6,960,671 B2 | 11/2005 | Cooker et al. | |
| 6,995,113 B1 | 2/2006 | Weisbeck et al. | |
| 7,057,056 B1 | 6/2006 | Qin et al. | |
| 2003/0148885 A1* | 8/2003 | Weisbeck et al. | 502/400 |
| 2004/0241502 A1 | 12/2004 | Chung et al. | |
| 2007/0027347 A1 | 2/2007 | Miller et al. | |
| 2008/0021230 A1* | 1/2008 | Qin et al. | 549/533 |

FOREIGN PATENT DOCUMENTS

| | | |
|---|---|---|
| BE | 1001038 A7 | 6/1989 |
| DE | 19959525 | 6/2001 |
| WO | WO 2005/092874 | 10/2005 |
| WO | WO 2009/005562 | 1/2009 |

OTHER PUBLICATIONS

New Developments in Selective Oxidation, G. Centi and F. Trifiro, Ed., pp. 33-38.
R. Szostak, "Non-aluminosilicate Molecular Sieves" in Molecular Sieves: Principles of Synthesis and Identification, (1989), pp. 205-281, Van Nostrand Reinhold.
G. Vayssilov, Catal. Rev.-Sci. Eng., vol. 39(3), (1997), pp. 209-251.
T. Maschmeyer et al., Nature, vol. 378(9), (1995) p. 159.
P.Tanev et al., Nature, vol. 368, (1994), p. 321.
A. Corma et al., J. Chem. Soc., Chem. Commun., (1998), p. 579.
D. Wei et al., Catal. Today, vol. 51, (1999), pp. 501-511.
K. Masters, Spray Drying in Practice, (2002), pp. 1-15, SprayDryingConsultant International AsP.
Y. Izumi et al., "Chapter 2 Clay as Potential Catalyst Material" in Zeolite,Clay, and Heteropoly Acid in Organic Reactions, (1992), pp. 49-97, Kodansha Ltd., Tokyo.
L. Hench, "Sol-Gel Technology", Kirk-Othmer Encyclopedia of Chemical Technology, On-Line Edition, (2008).
New Developments in Selective Oxidation, G. Centi and F. Trifiro, Ed., pp. 33-38, (1990).
T. Ban et al., J. Photochem. Photobiol. A: Chemistry, vol. 156, (2003), pp. 219-225.
J. Yang et al., Mater. Sci. Eng. C, vol. 15, (2001), pp. 183-185.

* cited by examiner

*Primary Examiner*—Bernard Dentz
*Assistant Examiner*—David E Gallis
(74) *Attorney, Agent, or Firm*—Yuanzhang Han

(57) ABSTRACT

A catalyst comprising a spray-dried transition metal zeolite and a noble metal is disclosed. The spray-dried transition metal zeolite comprises a transition metal zeolite and a binder. At least 50 wt. % of the binder is titania. The catalyst is used in a process to produce an epoxide by reacting an olefin, hydrogen, and oxygen. The catalyst is easy to filter from a slurry and produces a reduced level of hydrogenation products.

21 Claims, No Drawings

SPRAY-DRIED TRANSITION METAL ZEOLITE AND ITS USE

FIELD OF THE INVENTION

The invention relates to catalyst comprising a spray-dried transition metal zeolite and a noble metal. The catalyst is useful in producing an epoxide from an olefin, hydrogen, and oxygen.

BACKGROUND OF THE INVENTION

Transition metal zeolite catalysts have found increasing applications in chemical industry (see, e.g., *New Developments in Selective Oxidation*, G. Centi and F. Trifiro, Ed., pp. 33-38). They are often used in slurries, where their separations from liquids are necessary (U.S. Pat. Nos. 4,701,428, 5,354,875, 6,008,388, 6,106,803, 6,465,382, 6,958,405, and 7,057,056). When small crystals of a transition metal zeolite are used (e.g., smaller than 1 μm), their separations by filtration can be troublesome (see U.S. Pat. No. 6,960,671). To overcome the problem, transition metal zeolites have been formed into microspheres of greater sizes by spray drying method, where silica has been preferably used as the binder (U.S. Pat. Nos. 4,701,428, 4,954,653, 5,965,476, 6,106,803, and 6,524,984). However, attrition of these silica-bound microspheres often occurs during use; and fines generated can cause plugging of filters. It is desirable to produce transition metal zeolite catalysts that do not cause plugging of filters.

SUMMARY OF THE INVENTION

The invention is a catalyst comprising a spray-dried transition metal zeolite and a noble metal. The spray-dried transition metal zeolite comprises a transition metal zeolite and a binder. At least 50 wt. % of the binder is titania. The catalyst is used in a process to produce an epoxide by reacting an olefin, hydrogen, and oxygen.

DETAILED DESCRIPTION OF THE INVENTION

The invention is a catalyst comprising a spray-dried transition metal zeolite. The spray-dried transition metal zeolite comprises a transition metal zeolite. Zeolites are porous crystalline solids with well-defined structures. Generally they contain one or more of Si, Ge, Al, B, P, or the like, in addition to oxygen. Many zeolites occur naturally as minerals and are extensively mined in many parts of the world. Others are synthetic and are made commercially for specific uses. Zeolites have the ability to act as catalysts for chemical reactions which take place mostly within the internal cavities of the zeolites. Transition metal zeolites are zeolites comprising transition metals in framework. A transition metal is a Group 3-12 element. The first row of transition metals are from Sc to Zn. Preferred transition metals are Ti, V, Mn, Fe, Co, Cr, Zr, Nb, Mo, and W. More preferred are Ti, V, Mo, and W. Titanium zeolites are particularly preferred.

Preferred titanium zeolites are titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-82). Small amounts of impurities, e.g., boron, iron, aluminum, phosphorous, copper, and the like, and mixtures thereof, may be present in the lattice. The amount of impurities is preferably less than 0.5 wt. %, more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si to Ti in the lattice framework of the zeolite is advantageously from 9.5:1 to 99:1, most preferably from 9.5:1 to 60:1. Particularly preferred titanium silicates are titanium silicalites (see *Catal. Rev. Sci. Eng.*, 39(3) (1997) 209). Examples of titanium silicalites include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium silicates having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al., *Nature* 378(9) (1995) 159; Tanev, P. T., et al., *Nature* 368 (1994) 321; Corma, A., *J. Chem. Soc., Chem. Commun.* (1998) 579; Wei D., et al., *Catal. Today* 51 (1999) 501). The most preferred titanium zeolite is TS-1.

The spray-dried transition metal zeolite is formed by a spray drying method, which produces spherical particles out of a solution, a suspension, or a paste. Spray drying utilizes liquid atomization to create droplets which are dried to individual particles while moving in a gaseous medium (see Maters, K, *Spray Drying In Practice*, SprayDryConsultant International ApS (2002) pp. 1-15). Spray drying is known in forming zeolites, including titanium zeolites (see, e.g., U.S. Pat. Nos. 4,954,653, 4,701,428, 5,500,199, 6,524,984, and 6,106,803). Generally a spray dryer is used. A spray dryer is usually a large vertical chamber through which hot gas is blown and into which a solution, a suspension, or a pumpable paste is sprayed by a suitable atomizer. Particles produced by spray drying are generally from 5 μm to 1 mm in diameter.

A transition metal zeolite is generally prepared in the presence of an organic templating agent (see, e.g., U.S. Pat. No. 6,849,570). Suitable templating agents include alkyl amines, quaternary ammonium compounds, etc. When a zeolite is crystallized, it usually contains organic templating agent within its pores. Zeolites containing templating agents may be spray dried to produce the catalyst of the invention without being calcined first. Alternatively, a zeolite is calcined in an oxygen-containing atmosphere to remove the templating agent before it is spray dried.

The spray-dried transition metal zeolite comprises a binder. A binder helps to improve the mechanical strength and/or the physical properties of the spray-dried particles (e.g., crushing strength, surface area, pore size, pore volume). Sometimes the binder can modify the chemical properties (e.g., acidity, basicity) of the transition metal zeolite and its catalytic activity. Generally the binder constitutes from 1 to 90 wt. %, preferably 2 to 60 wt. %, more preferably from 5 to 50 wt. % of the catalyst. The concentration of the binder is defined as the weight percent of the non-zeolitic component of the spray-dried particles after the particles are calcined in an oxygen-containing atmosphere to remove the organic components.

At least 50 wt. %, preferably at least 80 wt. %, more preferably at least 95 wt. % of the binder is titania. Titania, or titanium dioxide, includes anatase and rutile. In addition to titania, the binder may include other metal oxides, non-metal oxides, mixed oxides, clays, and the like. They include silicas, aluminas, magnesias, silica-aluminas, montmorillonites, kaolins, bentonites, halloysites, dickites, nacrites, and anauxites, and the like, and mixtures thereof. Examples of clays can be found in "Chapter 2. Clay as Potential Catalyst Material," *Zeolite, Clay, and Heteropoly Acid in Organic Reactions* (1992) Kodansha Ltd., Tokyo.

One preferred method to preparing a suspension suitable for spray drying is to mix the transition metal zeolite, a titania sol, and optionally additional solvent. A sol is a colloidal suspension of solid particles in a liquid. In a sol, the thermal energy keeps the colloidal particles under constant and random agitation known as Brownian motion. This thermal driving force must be of a magnitude larger than the action of gravity, which means that each particle must have a very small mass. Colloidal particles are usually spherical or nearly spherical. Their sizes depend on the nature of the material, typically are <0.2 µm with metal or non-metal oxides. See Pierre, A. C., "Sol-Gel Technology," *Kirk-Othmer Encyclopedia of Chemical Technology*, on-line edition, 2008. A titania sol comprises a collection of small particles of titania (more accurately, hydrated titania) dispersed in a liquid phase.

Any titania sol may be used to prepare the catalyst. Many techniques have been used to prepare titania sols. See U.S. Pat. Nos. 4,612,138, 5,403,513, and 6,420,437; U.S. Pat. Appl. Pub. No. 2004/0241502; *J. Photochem. Photobiol. A* 156 (2003) 219. The method for preparing titania sols described in these references are incorporated herein by reference.

In one method, a titania sol is prepared by hydrolyzing a titania precursor in a solvent. Suitable solvents include water, alcohol, amide, nitriles, and the like, and mixtures thereof. Preferred solvents are water, alcohols, and their mixtures. A titania precursor is a compound that can be converted to titania by hydrolysis and/or calcination. Suitable titania precursors include titanium salts, titanium alkoxides, titanium oxyhalides, and the like. Examples of suitable titania precursors include titanium chloride, titanium sulfate, titanyl sulfate, titanyl oxosulfates, titanium tetramethoxide, titanium tetraethoxide, titanium tetraisopropoxide, titanium tetraisobutoxide, titanium tetra-tert-butoxide, titanium tetraphenoxide, titanium phenoxytrichloride, titanium triphenoxychloride, titanium acetylacetonate, titanium ethoxytrifluoride, titanium ethoxytrichloride, titanium ethoxytribromide, titanium diethoxydifluoride, titanium diethoxydichloride, titanium diethoxydibromide, titanium triethoxyfluoride, titanium triethoxychloride, titanium isobutoxytrichloride, and titanium diisobutoxydichloride.

A hydrolyzing agent, e.g., water, an acid or base is used to hydrolyze the titania precursor. Suitable acids include hydrochloric acid, hydrobromic acid, sulfuric acid, nitric acid, phosphoric acids, and carboxylic acids (e.g., formic acid, acetic acid, benzoic acid). Suitable bases useful as hydrolyzing agents include, e.g., sodium hydroxide, ammonium hydroxide, sodium carbonate, and sodium bicarbonate. Organic acids and bases are preferred hydrolyzing agents because they do not introduce hard-to-remove metal cations or inorganic anions.

A titania sol produced from the hydrolysis reaction may be used to prepare the catalyst without further processing. Alternatively, an amorphous titania, which may be isolated from the sol, is peptized in an organic base or acid solution. Peptization is a process of redistributing a flocculated colloid. It is used to disperse an amorphous precipitate into a colloidal sol. Peptization is known to modify the particles size and morphology of the particles in a sol. See *Mater. Sci. Eng. C* 15 (2001) 183. Suitable peptizing agents are those that interact strongly with titania precipitate and are able to bring charges onto the surface of the colloidal titania particles to stabilize the sol. Many organic amines and carboxylic acids, particularly those with bulky organic groups, may be used as peptizing agents. A peptizing agent brings in both steric and electric effect to stabilize the colloid. Preferred basic peptizing agents include t-butyl amine, diethyl amine, triethyl amine, isopropyl amine, and cyclohexyl amine. The preferred acidic peptizing agents include polyvalent carboxylic acids, hydroxy carboxylic acids (e.g., gluconic acid, glucolic acid, lactic acid, tartaric acid, citric acid, malic acid, succinic acid), and condensed phosphoric acids (e.g., pyrophosphoric acid, polyphosphoric acid).

A titania sol may be prepared directly from titania. Fine particles (<1 µm) of titania may be mixed with water, alcohol, or a mixture of both to form a titania sol.

In addition to a titania sol and a transition metal zeolite, the suspension suitable for spray drying may include other binders or binder precursors. A binder precursor is a compound that can be converted to a binder by hydrolysis and/or calcination. Examples of binder precursors include orthosilicic esters, alkoxysilanes, and alkoxyaluminates. Some specific examples of these are tetramethoxysilane, tetraethoxysilane, tetrapropoxysilane, tetrabutoxysilane, and analogous trialkoxyaluminium compounds.

The suspension suitable for spray drying typically contains from 50 to 90 wt. % solvent, from 1 to 40 wt. % transition metal zeolite, and from 1 to 40 wt. % titania. The amount of transition metal zeolite to titania is typically in the range of 95:5 to 5:95 in weight, preferably from 9:1 to 1:1.

The suspension is processed in a spray dryer. During spray-drying, the suspension is first broken down into fine droplets by an atomizing device, which are then fluidized and dried in a process gas (also called drying gas). Suitable atomizing devices are, for example, single-fluid pressure nozzles, two-fluid atomization nozzles, or rotary atomizers. The inlet temperature of the process gas may be between 100 and 700° C., preferably between 150 and 500° C.; the exit temperature of the process gas may be between 50 and 200° C., preferably between 80 and 160° C. The sprayed droplets are dried by the process gas to produce microspheres. The process gas and the droplets being spray-dried may be passed in the same or opposite directions.

Microspheres collected from a spray dryer may then be calcined at a temperature of between 200 and 1000° C., preferably between 400 and 700° C. Calcination may be performed in an inert gas. Nitrogen is one preferred inert gas. In one preferred method, the microspheres are calcined first in a nitrogen atmosphere, then in an oxygen-containing atmosphere.

The calcined microspheres generally have a mean mass diameter of 5 to 500 µm, preferably 20 to 80 µm. The particle size of the microspheres partly depends on the size of sprayed droplets and the proportion of solids in the suspension.

The catalyst comprises a noble metal. Suitable noble metals include gold, silver, platinum, palladium, iridium, ruthenium, osmium, rhenium, rhodium, and mixtures thereof. Preferred noble metals are Pd, Pt, Au, Re, Ag, and mixtures thereof. Palladium, gold, and their mixtures are particularly desirable. Typically, the amount of noble metal present in the catalyst will be in the range of from 0.01 to 20 wt. %, preferably 0.1 to 5 wt. %. In one particular embodiment, the catalyst comprises at least 0.01 wt. % palladium relative to the total weight of the catalyst.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium(0)).

The weight ratio of the transition metal zeolite to noble metal is not particularly critical. However, a transition metal zeolite to noble metal weight ratio of from 10:1 to 5,000:1 (grams of transition metal zeolite per gram of noble metal) is preferred.

The catalyst may comprise a promoter. A promoter helps to improve the catalyst performance (e.g., activity, selectivity, life of the catalyst). Preferred promoters include lead, bismuth, zinc, alkaline earth metals, lanthanide metals, and the like, and mixtures thereof. Particularly preferred promoters are selected from the group consisting of lead, bismuth, and mixtures thereof. The promoter may be added on the catalyst by the similar methods as used for adding the noble metal. While the choice of compound used as the promoter source is not critical, suitable compounds include metal carboxylates (e.g., acetate), halides (e.g., chlorides, bromides, iodides), nitrates, sulfate, and the like. The typical amount of promoter metal present in the catalyst will be in the range of from about 0.001 to 5 weight percent, preferably 0.001 to 2 weight percent relative to the catalyst.

The method in which the noble metal is incorporated in the catalyst is not critical. In one method, the noble metal may be incorporated as the transition metal zeolite is spray-dried. For example, a suitable noble metal source may be added to the slurry containing the titania sol and the transition metal zeolite and the slurry is spray dried into microspheres. In another method, the spray-dried transition metal zeolite is formed first and the noble metal is incorporated later. Many techniques may be used to add the noble metal, including, e.g., impregnation, adsorption, ion-exchange, and precipitation.

The invention also includes an epoxidation process comprising reacting an olefin, hydrogen, and oxygen in the presence of the catalyst.

An olefin is used in the process. Suitable olefins include any olefin having at least one carbon-carbon double bond, and generally from 2 to 60 carbon atoms. Preferably the olefin is an acyclic alkene of from 2 to 30 carbon atoms; the process is particularly suitable for epoxidizing $C_2$-$C_6$ olefins. More than one double bond may be present in the olefin molecule, as in a diene or triene. The olefin may be a hydrocarbon or may contain functional groups such as halogen, carboxyl, hydroxyl, ether, carbonyl, cyano, or nitro groups, or the like. In a particularly preferred process, the olefin is propylene and the epoxide is propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2:O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas is preferably used in the process. Any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of inert gases can also be used. The molar ratio of olefin to gas is usually in the range of 100:1 to 1:10 and especially 20:1 to 1:10.

The process may be performed in a continuous flow, semi-batch, or batch mode. A continuous flow process is preferred.

It is advantageous to work at a pressure of from 15 to 3,000 psig. The process is carried out at a temperature effective to achieve the desired olefin epoxidation, preferably at temperatures in the range of 0-200° C., more preferably, 20-150° C. Preferably, at least a portion of the reaction mixture is a liquid under the reaction conditions.

A reaction solvent is preferably used in the process. Suitable reaction solvents are liquid under the reaction conditions. They include, for example, oxygen-containing hydrocarbons such as alcohols, aromatic and aliphatic solvents such as toluene and hexane, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof.

Where a reaction solvent is used, it may be advantageous to use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphates, and ammonium hydroxide. The ammonium phosphate buffer is particularly preferred.

Following examples illustrate the invention.

EXAMPLE 1

Spray-Dried TS-1 with Titania Binder

Titanium silicalite-1 (TS-1) is prepared by following procedures disclosed in U.S. Pat. Nos. 4,410,501 and 4,833,260, but not calcined.

A transparent titania sol is prepared by following a procedure disclosed in *J. Photochem. Photobiol. A* 156 (2003) 219. An aqueous slurry is prepared by mixing non-calcined TS-1 (250 g), titania sol prepared above (1041 g), and de-ionized water (427 g). The slurry is spray dried with a Mobile Minor Spray Dryer (Niro Inc.) configured for a two-point powder discharge and a rotary atomizer. The drying chamber has an inside diameter of 2.7 feet and a 2-feet cylindrical height and a 60-degree angle conical bottom. A Watson Marlow peristaltic pump (model 521CC) is used to feed the slurry to the atomizer wheel and control the exit temperature. The main product is collected at the bottom port of the drying chamber and fines are routed to a cyclone collector. Nitrogen is used as drying/carrier gas at a flow rate of 80 kg/h. The inlet temperature is set at 220° C. The atomizer wheel is set at 27,000 RPM. A Watson Marlow peristaltic pump is used to evaporate water and control the exit temperature of the drying chamber to 95° C. The product is collected at the bottom of the drying chamber. Its mean mass diameter is 28 μm. The spray-dried TS-1 is calcined in air at 550° C. The calcined spray-dried TS-1 contains about 70% wt. % TS-1 and about 30 wt. % titania binder.

COMPARATIVE EXAMPLE 2

Spray-Dried TS-1 with Silica Binder

Spray-dried TS-1 is prepared by following procedures disclosed in U.S. Pat. Appl. Pub. No. 20070027347 with the exception that zinc oxide is not used. The spray-dried TS-1 is calcined in air at 550° C. The calcined spray-dried TS-1 contains approximately 80 wt. % TS-1 and 20 wt. % silica. Its mean mass diameter is 31 μm.

EXAMPLE 3

Pd-On-Titania Bound TS-1 (Catalyst A)

A sample of spray-dried TS-1 with titania binder prepared in Example 1 (16 g) is impregnated with an aqueous palladium tetraammine dinitrate solution (5.37 wt. % Pd) at 30° C. The slurry pH is adjusted to 7.6. The solids are filtered, dried, then calcined at 300° C. in air for 3 h. The calcined solids are transferred to a quartz tube and treated with a 4 vol. % hydrogen-in-nitrogen stream (100 mL/h) at 100° C. for 3 h. The material obtained (Catalyst A) contains 0.1 wt. % Pd.

COMPARATIVE EXAMPLE 4

Pd-ON-Silica Bound TS-1 (Catalyst B)

The procedure of Example 3 is repeated except that a spray-dried TS-1 with silica binder prepared in Example 2 is used. The material obtained (Catalyst B) contains 0.1 wt. % Pd.

EXAMPLE 5

Pd/Au-On-Titania Bound TS-1 (Catalyst C)

A solution is prepared by mixing $Na_2PdCl_4$ (19.9 wt. % Pd, 0.05 g), an aqueous $NaAuCl_4$ solution (20.74 wt. % Au, 0.048 g), and de-ionized water (30 g). The solution is combined with a spray-dried TS-1 prepared in Example 1 (18 g). $NaHCO_3$ powder is added to adjust the pH to 7.1. The slurry is stirred at 40° C. for 4 h. The solids are filtered, washed with de-ionized water (100 g×2), then dried. After the solids are calcined at 300° C. in air, they are washed with more de-ionized water (30 g×6) to remove residual chloride. The solids are calcined at 550° C. in air for 4 h. The calcined solids are transferred to a quartz tube and treated with a 4 vol. % hydrogen-in-nitrogen stream (100 mL/h) at 100° C. for 3 h. The catalyst obtained (Catalyst C) contains 0.05 wt. % Pd and 0.04 wt. % Au.

COMPARATIVE EXAMPLE 6

Pd/Au-On-Silica Bound TS-1 (Catalyst D)

The procedure of Example 3 is repeated except that a spray-dried TS-1 with silica binder prepared in Example 2 is used. The material obtained (Catalyst D) contains 0.05 wt. % Pd and 0.05 wt. % Au.

EXAMPLE 7

Propylene Epoxidation with Catalyst A

An ammonium dihydrogen phosphate solution is prepared by dissolving ammonium dihydrogen phosphate (5.75 g) in de-ionized water (250 g) and methanol (750 g).

A 300-mL stainless steel reactor is charged with Catalyst A (3.0 g) and ammonium dihydrogen phosphate solution prepared above (100 mL). The slurry in the reactor is heated to 50° C. under about 300 psig, and is stirred at 800 rpm. Additional ammonium dihydrogen phosphate solution is pumped to the reactor at a rate of about 50 g/h. The feed gas flow rates are about 4500 sccm (standard cubic centimeters per minute) for 5 vol. % oxygen in nitrogen, 280 sccm for propylene, and 110 sccm for hydrogen. The pressure in the reactor is maintained at 300 psig via a back pressure regulator with the feed gases pass continuously through the reactor. The gaseous effluent is analyzed by an on-line gas chromatograph (GC). The liquid is analyzed by an off-line GC every 12 h. The test lasts for 90 h. The products formed include propylene oxide (PO), propane, and derivatives of propylene oxide such as propylene glycol, propylene glycol monomethyl ethers, dipropylene glycol, and dipropylene glycol methyl ethers. The calculated results are shown in Table 1. The catalyst productivity is defined as the grams of PO formed (including PO which is subsequently reacted to form PO derivatives) per gram of catalyst per hour. POE (mole)=moles of PO+moles of PO units in the PO derivatives. PO/POE=(moles of PO)/(moles of POE)×100. Propylene to POE selectivity=(moles of POE)/(moles of propane formed+moles of POE)×100. Propylene to propane selectivity=(moles of propane)/(moles of propane formed+moles of POE)×100.

Though some catalyst breakage occurs during the reaction, the catalyst can be easily filtered. No plugging of filters is observed. The SEM image shows that some catalyst particles break into chunks without producing appreciable amount of catalyst dust.

COMPARATIVE EXAMPLE 8

Propylene Epoxidation with Catalyst B

The procedure of Example 7 is repeated except that Catalyst B is used instead of Catalyst A. Test results are shown in Table 1.

Some filter plugging is observed. The SEM image of the used catalyst shows that some dust is formed due to catalyst attrition.

EXAMPLE 9

Propylene Epoxidation with Catalyst C

The procedure of Example 7 is repeated except that Catalyst C is used instead of Catalyst A. Test results are shown in Table 2.

Similar to Example 7, though some catalyst breakage occurs during the reaction, the catalyst can be easily filtered. No plugging of filters is observed. The SEM image shows that some catalyst particles break into chunks without producing appreciable amount of catalyst fines.

COMPARATIVE EXAMPLE 10

Propylene Epoxidation with Catalyst D

The procedure of Example 7 is repeated except that Catalyst D is used instead of Catalyst A. Test results are shown in Table 2.

Similar to Example 8, some filter plugging is observed. The SEM image of the used catalyst shows that some dust is formed due to catalyst attrition.

Tables 1 and 2 show that a titania-bound TS-1 catalyst containing a noble metal produces much less propane (hydrogenation product) in the propylene epoxidation reaction than a silica-bound catalyst does under similar reaction conditions.

TABLE 1

| | Example | |
|---|---|---|
| | 7 | C. 8 |
| Catalyst | A | B |
| Catalyst Productivity, g POE/g cat/h | 0.41 | 0.34 |
| Propylene to POE Selectivity, % mole/mole | 91 | 76 |
| Propylene to Propane Selectivity, % mole/mole | 9 | 24 |
| PO/POE, mole/mole | 94 | 94 |

TABLE 2

| | Example | |
|---|---|---|
| | 9 | C. 10 |
| Catalyst | C | D |
| Catalyst Productivity, g POE/g cat/h | 0.17 | 0.18 |
| Propylene to POE Selectivity, % mole/mole | 98 | 77 |
| Propylene to Propane Selectivity, % mole/mole | 2 | 23 |
| PO/POE, mole/mole | 98 | 96 |

We claim:

1. A catalyst comprising a spray-dried transition metal zeolite, and a noble metal, wherein the spray-dried transition metal zeolite comprises a transition metal zeolite and an inorganic binder, at least 50 wt. % of said binder which is titania.

2. The catalyst of claim 1 wherein at least 80 wt. % of the binder is titania.

3. The catalyst of claim 1 wherein at least 95 wt. % of the binder is titania.

4. The catalyst of claim 1 wherein the transition metal zeolite is a titanium zeolite.

5. The catalyst of claim 1 wherein the transition metal zeolite is TS-1.

6. The catalyst of claim 1 wherein the noble metal is selected from the group consisting of gold, silver, platinum, palladium, iridium, ruthenium, rhenium, rhodium, osmium, and mixtures thereof.

7. The catalyst of claim 1 wherein the noble metal is selected from the group consisting of palladium, gold, and mixtures thereof.

8. The catalyst of claim 1 wherein the noble metal is palladium.

9. The catalyst of claim 1 having a mean mass diameter of 20 to 80 μm.

10. The catalyst of claim 1 further comprising a promoter selected from the group consisting of lead, bismuth, and mixtures thereof 11. An epoxidation process comprising reacting an olefin, hydrogen, and oxygen in a solvent in the presence of the catalyst of claim 1.

12. The process of claim 11 wherein at least 80 wt. % of the binder is titania.

13. The process of claim 11 wherein at least 95 wt. % of the binder is titania.

14. The process of claim 11 wherein the transition metal zeolite is a titanium zeolite.

15. The process of claim 11 wherein the transition metal zeolite is TS-1.

16. The process of claim 11 wherein the noble metal is selected from the group consisting of gold, silver, platinum, palladium, iridium, ruthenium, rhenium, rhodium, osmium, and mixtures thereof.

17. The process of claim 11 wherein the noble metal is selected from the group consisting of palladium, gold, and mixtures thereof.

18. The process of claim 11 wherein the noble metal is selected from the group consisting of palladium, gold, and mixtures thereof.

19. The process of claim 11 wherein the noble metal is palladium.

20. The process of claim 11 wherein the catalyst comprises a promoter selected from the group consisting of lead, bismuth, and mixtures thereof.

21. A continuous process of claim 11.

* * * * *